ical Chemistry, 1973, pp. 2040-2043, vol. 248, No. 6, American
(12) United States Patent
Araki et al.

(10) Patent No.: US 7,629,457 B2
(45) Date of Patent: *Dec. 8, 2009

(54) METHOD FOR PRODUCING CYTOSINE NUCLEOSIDE COMPOUNDS

(75) Inventors: Tadashi Araki, Chiba (JP); Ichirou Ikeda, Chiba (JP); Kaori Matoishi, Chiba (JP); Reiko Abe, Chiba (JP); Toshihiro Oikawa, Chiba (JP); Yasuko Matsuba, Fukuoka (JP); Hiroki Ishibashi, Fukuoka (JP); Kiyoteru Nagahara, Fukuoka (JP); Yasushi Fukuiri, Fukuoka (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/967,239

(22) Filed: Oct. 19, 2004

(65) Prior Publication Data

US 2005/0233420 A1 Oct. 20, 2005

Related U.S. Application Data

(62) Division of application No. 10/134,624, filed on Apr. 30, 2002, now Pat. No. 6,858,721.

(30) Foreign Application Priority Data

May 1, 2001 (JP) ............................. 2001-134352

(51) Int. Cl.
*C07H 21/00* (2006.01)
*C07H 21/02* (2006.01)
*C07H 21/04* (2006.01)

(52) U.S. Cl. ..................... 536/25.3; 536/22.1; 536/26.1; 536/26.8; 435/87; 435/89

(58) Field of Classification Search ................ 536/22.1, 536/26.1, 26.8, 25.3; 435/87, 89
See application file for complete search history.

(56) References Cited

U.S. PATENT DOCUMENTS 4,839,285 A 6/1989 Asahi et al.

5,258,301 A 11/1993 Yamauchi et al.
5,814,639 A * 9/1998 Liotta et al. ................. 514/274

FOREIGN PATENT DOCUMENTS

| EP | 0 896 065 A1 | 2/1999 |
|---|---|---|
| EP | 1 179 598 A1 | 2/2002 |
| JP | 64-060396 | 3/1989 |
| JP | 01060396 | 3/1989 |
| JP | 01-104190 | 4/1989 |
| JP | 03-127986 | 5/1991 |
| JP | 11-137290 | 5/1999 |
| WO | 00/70074 A1 | 11/2000 |
| WO | 01/14566 A2 | 3/2001 |

OTHER PUBLICATIONS

European Search Report for EP 02 25 3075 dated May 16, 2003.
Hershfield et al., "*Use of Site-Directed Mutagenesis to Enhance the Epitope-Shielding Effect of Covalent Modification of Proteins with Polyethylene Glycol*", Proc. Natl. Acad. Sci. USA, 1991, pp. 7185-7189, vol. 88, National Academy of Sciences, Washington, D.C., USA.
Ling et al., "*Purification and Characterization of a Novel Nucleoside Phosphorylase from a Klebsiella sp. and its Use in the Enzymatic Production of Adenine Arabinoside*", Applied and Environmental Microbiology, 1990, pp. 3830-3834, vol. 56, No. 12, American Society for Microbiology, Washington, D.C., USA.
Hoffee et al., "*Thymidine Phosphorylase from Salmonella typhimurium*", Methods in Enzymology, 1978, pp. 437-443, vol. LI, Academic Press, Inc., New York, New York, USA.
Robertson et al., "*Purification and Properties of Purine Nucleoside Phosphorylase from Salmonella typhimurium*", The Journal of Biological Chemistry, 1973, pp. 2040-2043, vol. 248, No. 6, American Society for Biochemistry and Molecular Biology, Baltimore, Maryland, USA.

* cited by examiner

*Primary Examiner*—Patrick T Lewis
(74) *Attorney, Agent, or Firm*—Buchanan Ingersoll & Rooney PC

(57) ABSTRACT

The invention provides a method for producing a cytosine nucleoside compound from pentose-1-phosphate and cytosine or a derivative thereof using a nucleoside phosphorylase reactive to cytosine or a bacterium having the enzyme activity. The invention also provides a method for specifically reducing an activity to degrade the substrates or the product, resulting in efficient production of the cytosine nucleoside compound. According to the invention, little by-product is produced in producing cytonucleocide compounds.

3 Claims, 3 Drawing Sheets

M: Molecular weight markers
1: Crude enzyme solution
2: DEAE-Toyopearl
3: Hydroxyapatite

METHOD FOR PRODUCING CYTOSINE NUCLEOSIDE COMPOUNDS

This application is a division of application Ser. No. 10/134,624, filed on Apr. 30, 2002, now U.S. Pat. No. 6,858,721, which claims priority under 35 U.S.C. § 119 to Application No. 2001-134352, filed in Japan on May 1, 2001; the entire content of which is hereby incorporated by reference.

BACKGROUND OF THE INVENTION

1. Field of the Invention

The present invention relates to a method for producing cytosine nucleoside compounds, which are useful as starting material for synthesis of compounds, such as those for medical use. More specifically, the invention relates to a method for producing cytosine nucleoside compounds from pentose-1-phosphate and cytosine or a cytosine derivative, by using an enzyme with cytosine-nucleoside phosphorylase activity, microbial cells with the enzyme activity, an enzyme preparation from the microbial cells or the culture thereof, or the like.

2. Description of the Related Art

Nucleoside phosphorylases generally refer to enzymes which phosphorolyze the N-glycoside bond of a nucleoside in the presence of phosphoric acid, and in the case where ribonucleoside is used, catalyze a reaction represented by the following equation:

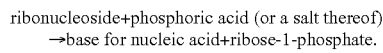
ribonucleoside+phosphoric acid (or a salt thereof)
→base for nucleic acid+ribose-1-phosphate.

Those enzymes, roughly divided into purine-nucleoside phosphorylases and pyrimidine-nucleoside phosphorylases, are distributed in a wide variety of living organisms, such as tissues including those of mammals, birds or fish, yeast or bacteria. These enzyme reactions are reversible, and synthesis of different nucleosides thus utilizing the reverse rections has been known. For example, there are known methods for production of thymidine (Japanese Patent Laid-Open No. 01-104190), 2'-deoxuadenosine (Japanese Patent Laid-Open No. 11-137290) or 2'-deoxyguanosine (Japanese Patent Laid-Open No. 11-137290), respectively, from 2'-deoxyribose-1-phosphate and a base for nucleic acid (thymine, adenine or guanine). Thus, production of a nucleoside using a phosphorylase can be produced regio-specifically and stereo specifically in a mild condition, and many nucleoside compounds are studied for synthesis.

Japanese Patent Laid-Open No. 1-60396 describes a process for production of deoxycytidine by the reaction of deoxyribose-1-phosphate with cytosine using bacterial cells themselves as catalyst. Though the process of the application uses bacterial cells per se as reaction catalyst, it is uncertain whether cytosine-nucleoside phosphorylase itself may exist therein. There is a possibility such that deoxycytidine accumulated in the bacterial cells may have leached out of the cells during the reaction, or that nucleoside deoxyribosyl transferase within the cells may have transferred cytosine added as substrate to the base of deoxynucleoside within the cells, resulting in detection of deoxycytidine. The inventors sent for the seven bacterial strains that have been deposited for the examples of the application, and tested the production of deoxycytidine from deoxyribose-1-phosphate and cytosine according to the examples. As a result, deoxycytidine could not be detected in the solution of the reaction using any one of the strains, indicating that enzyme activity corresponding to cytosine-nucleoside phosphorylase was not present in the strains themselves.

On the other hand, Japanese Patent Laid-Open No. 3-127986 describes a novel nucleoside phosphorylase acting on both purine and pyrimidine bases, where the pyrimidine base is deoxyuridine, deoxycytidine or deoxythymidine, but no substrate specificity of the enzyme is disclosed in the specification. Further, the application has already been withdrawn and therefore the enzyme activity cannot be characterized any more. The inventors of the application, however, purified a nucleoside phosphorylase from the strain of the same designation as that disclosed in the application, and reported the characteristics thereof in Applied and Environmental Microbiology, Vol. 56, pp. 3830-3834 (1990). The article states that the above enzyme has no activity to cytosine, cytidine of deoxycytidine.

Apart from the enzyme described above, it is not known that cytosine or any derivative thereof may be a substrate for either purine nucleoside phosphorylase or pyrimidine nucleoside phosphorylase. For example, thymidine nucleoside phosphorylase, one of pyrimidine nucleoside phosphorylases, derived from Salmonera typhimurium described in Method. Enzymology, Vol. 51, pp. 437-442 (1978) has no activity to deoxycytidine. In addition, it is reported in J. Biol. Chem., Vol. 248, No. 6, pp. 2040-2043 (1973) that purine nucleoside phosphorylase derived from Salmonera typhimurium has no activity to pyrimidine nucleoside, such as uridine, cytidine, deoxyuridine or deoxycytidine.

When these publications are totally considered, an enzyme corresponding to cytosine nucleoside phosphorylase related to the present invention may have been existent, but none of those preceding publications could confirm it and actually obtain the enzyme.

SUMMARY OF THE INVENTION

Production of a nucleoside compound using nucleoside phosphorylase enables the nucleoside to be synthesized both regiospecifically and stereo specifically under mild conditions, thereby prompting synthetic studies of various nucleoside compounds. However, no isolated and purified nucleoside phosphorylase has ever been reported that is able to synthesize a cytosine nucleoside compound from cytosine or a derivative thereof and sugar phosphate as substrate.

Also, the inventors have found that if bacterial cells per se are used, or if an enzyme preparation for use, prepared from bacterial cells and/or culture broth thereof, has the remainder of cytosine or cytidine deaminase activity, which is generally present in the cells, both cytosine or the derivative thereof as substrate and the cytosine nucleoside compound as product may be deaminated, thereby making efficient accumulation of the cytosine nucleoside compound difficult.

One object of the present invention is thus to provide the amino acid sequence of a nucleoside phosphorylase capable of synthesizing a cytosine nucleoside compound. Another object of the present invention is to provide a recombinant plasmid containing the corresponding gene, a transformant carrying the recombinant plasmid, a method for producing the enzyme using the transformed bacterial strain and a method for producing a cytosine nucleoside compound using the transformed bacterial strain. Another object of the present invention is to provide a method for reducing cytosine or cytidine deaminase activity, while keeping the activity of the nucleoside phosphorylase, or to provide a method for efficiently producing a cytosine nucleoside compound by using a bacterial strain having expressed cytosine nucleoside phosphorylase in another bacterial strain devoid of both deaminase.

Another object of the present invention is to provide a method for reducing the activity of an enzyme capable of dephosphorylating sugar phosphate as starting material, or to provide a method for efficiently producing a cytosine nucleoside compound by using a bacterial strain having expressed cytosine nucleoside phosphorylase in another bacterial strain devoid of the enzyme.

In the production of a cytosine nucleoside compound, especially for preparing a pharmaceutical product, mixing even a minute amount of a byproduct therein may cause a serious problem. In the purification step, separation of the byproduct nucleoside from the cytosine nucleoside compound may impose a heavy burden on the step as well as decrease the recovery of the compound, which will be a serious problem in case of commercial production. In the case where the compound is to be used for such a purpose, it is required to eliminate cytosine or cytidine deaminase activity from the enzyme preparation as completely as possible.

The inventors addressed themselves to solving these subjects, resulting in the unexpected finding that a purine nucleoside phosphorylase, which in itself should catalyze a reaction involving purine base as substrate, is able to catalyze a reaction for producing a cytosine nucleoside compound from cytosine or a derivative thereof, which is a sort of pyrimidine base, and pentose-1-phosphate.

The presence of the purine nucleoside phosphorylase that the inventors found also indicates the presence of cytosine nucleoside phosphorylase.

However, the reaction of cytosine or a derivative thereof with pentose-1-phosphate in the presence of the bacterium having this enzyme activity was found to produce almost exclusively the deaminated products of cytosine or the derivative thereof and the cytosine nucleoside compound, thus failing in efficient accumulation of the cytosine nucleoside compound of interest. Intensive work revealed that formation of the deaminated products was due to the action of deaminases, and that the cytosine and cytidine deaminases could be deactivated by placing the bacterial cells in an organic solvent with or without stirring under still stand, or by heating them, and also that deactivation of cytosine nucleoside phosphorylase to be maintained could be controlled efficiently by addition of phosphate or sugar phosphate into the fluid to be processed.

It was now found possible, by means of the method described above, to reduce specifically decomposition of the substrate and/or the product with the activity of the nucleoside phosphorylase maintained, and to produce the cytosine nucleoside compound with little or no byproduct from cytosine or the derivative thereof and the sugar phosphate, by using the bacterial cells whose deaminase activity was previously eliminated or decreased by the processing as mentioned above. The finding is inventive.

The processing for eliminating or decreasing the deaminase activity according to the present invention may eliminate the decomposing activity almost completely, while the activity of the cytosine nucleoside phosphorylase can be maintained almost completely. Furthermore, it was also found possible to efficiently produce a cytosine nucleoside compound by expressing the phosphorylase in a bacterium devoid of both enzyme activities of cytosine and cytidine deaminases. The findings are inventive.

Also, the reaction yield was found to be lowered in the presence of an enzyme capable of dephosphorylating the sugar phosphate as starting material. The enzyme could be selectively deactivated by addition of a polar solvent to the disrupted cells of a bacterium having the enzyme activity. The enzyme activity could be also removed through a purification procedure for the cytosine nucleoside phosphorylase, such as fractionation by salting out or adsorption onto an ion-exchange resin carrier or the like. It was found that these treatments enabled a cytosine nucleoside compound to be produced efficiently. The finding is inventive. Further, expression of the cytosine nucleoside phosphorylase in a bacterium devoid of the dephosphorylating enzyme was found to efficiently produce the cytosine nucleoside compound. The findings are inventive.

The present invention provides a method for efficiently producing a cytosine nucleoside compound using cytosine nucleoside phosphorylase, which has never been attained.

The present invention is thus described as follows.

The method for producing a cytosine nucleoside compound according to the present invention is characterized by including a step wherein the cytosine nucleoside compound is obtained in the reaction of a sugar phosphate with cytosine or a derivative thereof in the presence of an enzyme with the activity of cytosine nucleoside phosphorylase.

The enzyme includes an enzyme with the activity of purine nucleoside phosphorylase, and thus an enzyme preparation containing the activity of purine nucleoside phosphorylase may be used appropriately in the method for producing the cytosine nucleoside compound of the present invention. An example of such enzyme with the activity of purine nucleoside phosphorylase is an enzyme derived from *Escherichia coli*.

The cytosine derivative described above is represented by formula (I) as follows:

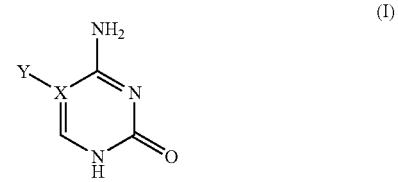

wherein X denotes a carbon or nitrogen atom, and Y is a hydrogen atom, a halogen atom or a lower alkyl group. Examples thereof are azacytosine and 5-fluorocytosine.

The enzyme with the activity of cytosine nucleoside phosphorylase as described above may be provided in the form of bacterial cells having the enzyme, or enzyme preparations including crude enzyme extract and purified enzyme preparation which can be obtained from the cells or the culture thereof into the reaction system.

The bacterial cells or enzyme preparation may be preferably devoid of cytosine and cytidine deaminase activities, or if they are present, so depleted as to be able to produce the cytosine nucleoside compound by means of the activity of cytosine nucleoside phosphorylase. As an example, the bacterial cells or enzyme preparation with a higher activity of cytosine nucleoside phosphorylase than cytosine and cytidine deaminase activities are suitable for use.

An example of such bacterial cells or enzyme preparation is one processed to reduce cytosine and cytidine deaminase activities that it has.

The processed bacterial cells as described above, where the deaminase activities have been lost or reduced, may be obtained, as an example, by contacting the bacterial cells having the activity of cytosine nucleoside phosphorylase with an aqueous solution containing organic solvent in order to reduce selectively cytosine and cytidine deaminase activities. The organic solvent includes a polar solvent such as an alcohol. The organic solvent may be at least one solvent selected from the group including, for example, methyl alcohol, ethyl alcohol, propyl alcohol, butyl alcohol, dioxane and acetone.

In addition, the concentration of the organic solvent in water may be preferably 20% (v/v) or more when the organic solvent eliminates or reduces the cytosine and cytidine deaminase activities.

On the other hand, the processed bacterial cells, where the deaminase activities have been lost or reduced, may also be obtained by heating the bacterial cells having the activity of cytosine nucleoside phosphorylase in an aqueous solution at such a temperature as to reduce selectively cytosine and cytidine deaminase activities. Heating may be conducted at 50° C. or higher for 10 minutes to 40 hours.

In addition, when the bacterial cells are processed so as to eliminate or reduce the deaminase activities, the presence of pentose-1-phosphate allows the activity of cytosine nucleoside phosphorylase to be maintained more efficiently. The concentration of pentose-1-phosphate may be preferably in the range from 1 mM to 100 mM.

DETAILED DESCRIPTION OF THE PREFERRED EMBODIMENTS

Figure 1:
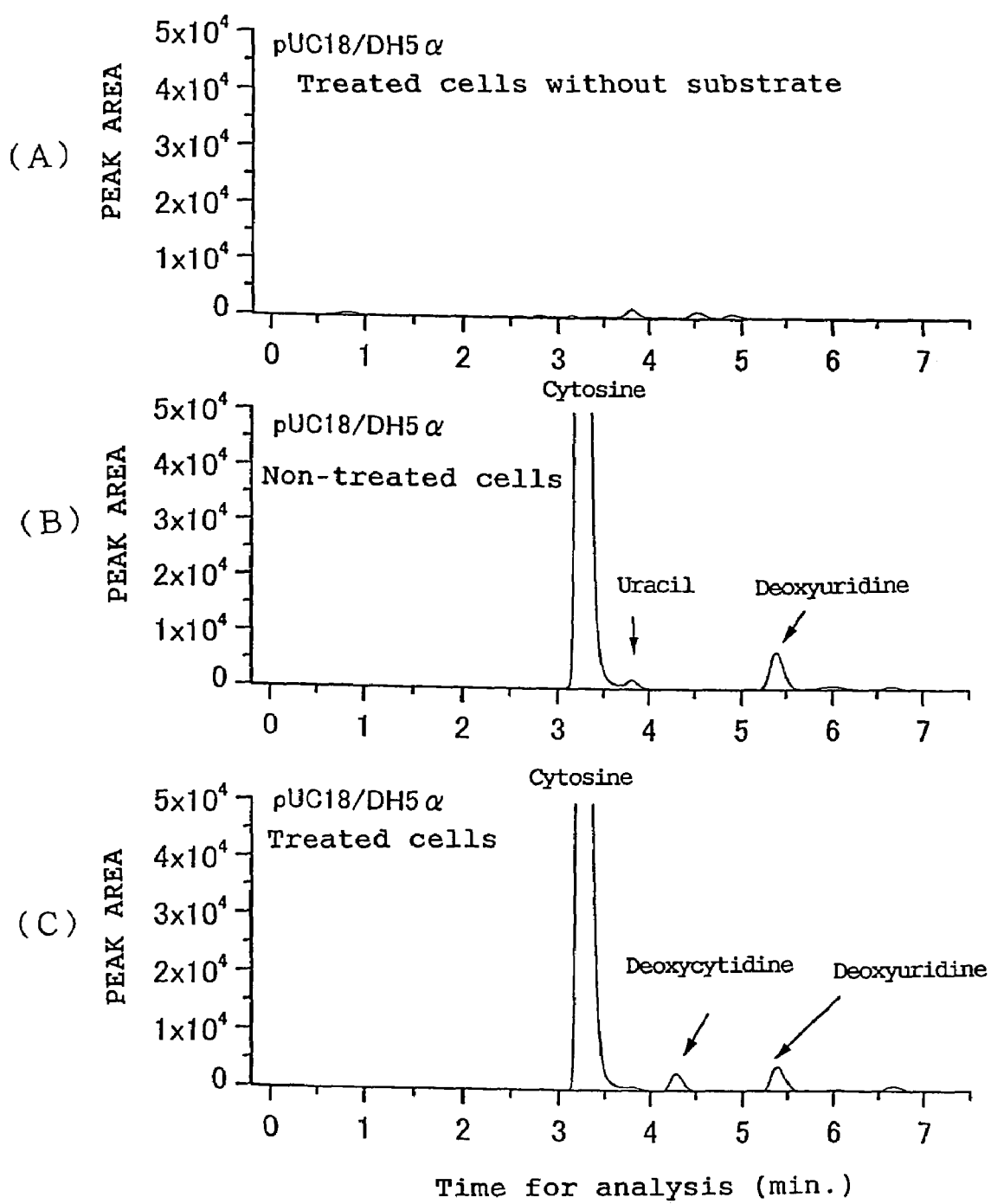
FIG. 1A shows an analytical chart of HPLC in the Comparative Example 1.
FIG. 1B shows an analytical chart of HPLC of a reaction solution in the Comparative Example 1.
FIG. 1C shows an analytical chart of HPLC of Example 6.

The term cytosine nucleoside phosphorylase refers to an enzyme able to produce a cytosine nucleoside compound from cytosine or a derivative thereof as substrate, and may be derived from any of an animal, a plant or a microbe if the requirement is satisfied. Generally, the enzyme termed cytosine nucleoside phosphorylase is unknown in the art. Therefore, this term is defined only in the present invention as mentioned above. A suitable example of such cytosine nucleoside phosphorylases is an enzyme conventionally known as purine nucleoside phosphorylase which bacteria belonging to genus *Escherichia*, such as *Escherichia coli* contain and having also the activity of cytosine nucleoside phosphorylase. As an embodiment, the DNA base sequence for the purine nucleoside phosphorylase of *Escherichia coli* is illustrated as SEQ ID NO: 3 and the amino acid sequence translated from the base sequence as SEQ ID NO: 4. Recent progress in genetic engineering has made it easier to modify an amino acid sequence by means of deactivation, insertion or substitution for a part of the base sequence. Such level of technology has enabled the amino acid sequence to be modified through modification of the part of the base sequence without affecting the desired enzyme activity, that is to say, with the enzyme activity maintained or even elevated, and the amino acid sequence thus modified is also included by the cytosine nucleoside phosphorylase according to the present invention. For example, an amino acid sequence modified from the amino acid sequence of SEQ ID NO: 4, wherein deletion, substitution or addition has occurred for 2 to 3 amino acids without affecting the enzyme activity of interest, and an amino acid sequence coded by a base sequence modified from the base sequence of SEQ ID NO: 3, where mutation such as deletion, substitution or addition has occurred without affecting the enzyme activity of interest, while the complementary sequence can hybridize under stringent conditions, may be used in the present invention.

If an enzyme has thus the activity of purine nucleoside phosphorylase, the enzyme alone can produce both purine-type and cytosine nucleoside compounds, thereby providing a great advantage for commercial production of nucleosides.

The enzyme with the activity of cytosine nucleoside phosphorylase used in the method of the present invention may be provided in the form of bacterial cells having the enzyme, or an enzyme preparation prepared from the cells or the culture thereof into the reaction system. This enzyme preparation includes the bacterial cells or the culture thereof processed variously, enzyme extract, the enzyme extract purified to some extent or as isolate and the like.

The bacterial cells or enzyme preparation may be one commercially available or prepared utilizing any of various methods. The preparation with the enzyme activity may be selected from, for example, a commercially available enzyme, bacterial cells with the enzyme activity and a preparation by cell treatment or an immobilized form thereof. Examples of the cell treatment preparation include acetone-dried cells and disrupted cells, cell debris, prepared by means of any treatment, such as mechanical disruption, ultrasonic disruption, freezing and thawing, pressurization and depressurization, osmotic shock, self-lysation, cell wall disintegration or surfactant treatment, and also a purified enzyme obtained by precipitation with ammonium sulfate or acetone, or by column chromatography, if necessary.

The bacterium with the activity of cytosine nucleoside phosphorylase is not limited in particular, if it expresses cytosine nucleoside phosphorylase able to produce a cytosine nucleoside compound from cytosine or a derivative thereof as substrate. Such a bacterium may be selected from, for example, common bacteria expressing nucleoside phosphorylase Suitable examples of such bacteria producing nucleoside phosphorylase are bacteria belonging to genus *Escherichia*, such as *Escherichia coli*. Recent progress in molecular biology and genetic engineering has made it possible and then easier to obtain the gene for the purine nucleoside phosphorylase from the bacterial strain via analysis of the molecular biological properties and amino acid sequence of the enzyme, then construct a recombinant plasmid where the gene and a regulator region for expressing it have been inserted, and then create a recombinant bacterium where the protein has been expressed, through transfer of the plasmid into any host bacterium. Considering such level of technology, a recombinant bacterium created by incorporation of the gene for the nucleoside phosphorylase into any host bacterium is also included in the bacterium expressing the activity of nucleoside phosphorylase according to the present invention.

The regulatory region necessary for the gene expression described herein includes a promoter sequence (including a operator sequence to control transcription), a ribosome-binding sequence (a SD sequence), and a transcription termination sequence. Examples of the promoter sequence may be a trp promoter that is a tryptophan operon derived from *E. coli*, a lac promoter as lactose operon, a PL or PR promoter derived from λ phage, a gluconate synthase promoter (gnt) derived from *Bacillus subtilis*, an alkaline protease promoter (apr), a neutral protease promoter (npr) and an α-amylase promoter (amy). Sequences specifically designed and modified, such as a tac promoter may also be used. Examples of the ribosome-binding sequence may be such sequences derived from *E. coli* or *B. subtilis*, but are not limited in particular provided that they function within a desirable host such as *E. coli* or *B. subtilis*. As an example, a consensus sequence where a sequence of 4 or more consecutive bases is complementary to the 3'-terminal region of a 16 S ribosomal RNA may be prepared in DNA synthesis, and then used for the purpose. The transcription termination sequence is not essential, but, if necessary, ones independent of the ρ factor, such as a lipoprotein terminator and a trp operon terminator can be used. These regulatory regions on the recombinant plasmid are preferably arranged in the order of the promoter sequence, the ribosome-binding sequence, the gene coding nucleoside phosphorylase and the transcription termination sequence, from the 5'-terminal on the upstream side.

Examples of the plasmid described herein that can be used as vector may be pBR322, pUC18, Bluescript II SK (+), pKK223-3 and pSC101 having a region in *E. coli* where it is able to self-replicate, and pUB110, pTZ4, pC194, ρ11, φ1 and φ105 having a region in *B. subtilis* where it is able to self-replicate. In addition, examples of the plasmid that is able to self-replicate in more than one bacterial strain and may be used as vector are pHV14, TRp7, YEp7 and pBS7.

Any bacterial host described herein includes *Escherichia coli* as typical example which will be described below in the Examples, but is not limited to *E. coli* in particular and also includes other microbial strains, such as bacteria belonging to Genus *Bacillus* such as *Bacillus subtilis*, yeasts and actinomycetes.

The cytosine nucleoside compound according to the present invention refers to a compound where a sugar phosphate and cytosine or a derivative thereof as base of nucleic acid are bound together via a N-glycoside bond. Its typical examples are cytidine, deoxycytidine, dideoxycytidine, azacytidine, deoxyazacytidine, 5-fluorocytidine and 5-fluorodeoxycytidine, but not limited to these compounds.

The cytosine derivative according to the present invention refers to a compound which has a cytosine structural moiety convertible to a cytosine nucleoside structure by the action of cytosine nucleoside phosphorylase. Preferable examples of the cytosine derivative are cytosine derivatives represented by the general formula (I) described above. As the lower alkyl group of Y in the general formula (I), an alkyl group having 1 to 4 carbon atoms such as a methyl group, an ethyl group, a propyl group, an isopropyl group, a n-butyl group, a sec-butyl group and a tert-butyl group. Among the cytosine derivatives, for example, azacytosine, 5-fluorocytosine and 5-methylcytosine are particularly preferred.

The sugar phosphate according to the present invention refers to a polyhydroxyaldehyde, a polyhydroxyketone or a derivative thereof whose position 1 is esterified with phosphoric acid. Typical examples thereof are preferably ribose 1-phosphate, 2'-deoxyribose 1-phosphate, 2',3'-di deoxyribose 1-phosphate, arabinose 1-phosphate and dioxolane-type sugar phosphate.

The polyhydroxyaldehyde or polyhydroxyketone derived from natural products includes an aldopentose such as D-arabinose, L-arabinose, D-xylose, L-lyxose or D-ribose, a ketopentose such as D-xylulose, L-xylulose or D-ribulose, a deoxysugar such as D-2-deoxyribose or D-2,3-dideoxyribose, or the like, but is not limited to these.

These sugar phosphates can be prepared by the method wherein they are produced by phosphorolysis of nucleoside compounds with nucleoside phosphorylase (J. Biol. Chem. Vol. 184, 437, 1950), or also by methods of chemical synthesis selective to the anomers.

Furthermore, the method of enzymatic synthesis for deoxyribose 1-phosphate as described in WO 01/14566 may be utilized. (The route for synthesis of deoxyribose 1-phosphate according to the patent assigned to Roche Ltd. is also referred to therein.)

The processing for reducing cytosine and cytidine deaminase activities according to the present invention is not limited in particular, provided that the deaminase activities can be eliminated or reduced without deactivating nucleoside phosphorylase, but a suitable processing is exemplified by exposure of the bacterial cells, their culture or the processed material thereof to an organic solvent, or heat treatment of any one of the above.

The organic solvent according to the present invention may be any solvent capable of eliminating cytosine and cytidine deaminase activities. The organic solvent includes, but is not limited to, a polar solvent, such as methyl alcohol, ethyl alcohol, propyl alcohol, butyl alcohol, dioxane, tetrahydrofuran, methyl ethyl ketone or acetone; an alcohol, such as 1-hexanol, 2-methyl-1-pentanol, 4-methyl-2-pentanol, 2-ethyl-1-butanol, 1-heptanol, 2-heptanol, 3-heptanol, 1-octanol, 2-octanol or 1-nonanol; an ester, such as propyl acetate, butyl acetate, isobutyl acetate, sec-butyl acetate, pentyl acetate, isopentyl acetate, cyclohexyl acetate or benzyl acetate; a hydrocarbon, such as pentane, hexane, 2-methylhexane, 2,2-dimethylbutane, 2,3-dimethylbutane, cyclohexane, methylcyclohexane, heptane, cycloheptane, octane, cyclooctane, isooctane, nonane, decane, dodecane, petroleum ether, petroleum benzin, ligroin, industrial gasoline, kerosene, benzene, toluene, xylene, ethylbenzene, propylbenzene, cumene, mesitylene or naphthalene; a halogenated hydrocarbon, such as dichloromethane, chloroform, carbon tetrachloride, dichloroethane, chlorobenzene or dichlorobenzene; a phenol, such as cresol or xylenol; a ketone, such as methyl isobutyl ketone or 2-hexanone; and an ether, such as dipropyl ether, diisopropyl ether, diphenyl ether and dibenzyl ether; and also a hydrocarbon, such as pentane, hexane, heptane, octane, cyclopentane, cyclohexane, cycloheptane, cyclooctane, toluene or ethylbenzene. Among other organic solvents used in the present invention are amide compounds, such as N,N-dimethylformamide, N,N-dimethylacetamide, N,N-dimethylbenzamide, N-methyl-2-pyrrolidone, N-methylformamide, N-ethylformamide, N-methylacetamide, formamide, acetamide and benzamide, urea compounds, such as urea, N,N'-dimethylurea, tetramethylurea and N,N'-dimethylimidazolidinone, and sulfoxide compounds, such as dimethyl sulfoxide, diethyl sulfoxide and diphenyl sulfoxide.

The processing with the organic solvent for eliminating or reducing deaminase activities according to the present invention is not limited in particular, provided that cytosine and cytidine deaminase activities can be eliminated or reduced without deactivating nucleoside phosphorylase, but a suitable processing is conducted under conditions where the bacterial cells, their culture or the processed material thereof is kept standstill or suspended at pH 4.0 to 10.0, preferably pH 6.0 to 9.0, at the concentration of the organic solvent in water not less than 10% by volume, preferably not less than 20% by volume, more preferably not less than 30% by volume, at a temperature not lower than 0° C., preferably ranging from 20° C., preferably 50° C., to 80° C., for 10 minutes or more, preferably up to 40 hours, more preferably for 1 to 20 hours.

Further, addition of the sugar phosphate at not less than 1 mM, preferably at not more than 100 mM, to the above processed fluid can make the nucleoside phosphorylase more stable.

Addition of the organic solvent into the reaction solution may be also effective similarly.

Heat treatment according to the present invention is not limited in particular, provided that cytosine and cytidine deaminase activities can be eliminated or reduced without deactivating nucleoside phosphorylase, but a suitable heat treatment is conducted under conditions where the bacterial cells, their culture or the processed material thereof is kept standstill or suspended in an aqueous medium at pH 4.0 to 10.0, preferably pH 6.0 to 9.0, at a temperature not lower than 50° C., preferably ranging from 60 to 80° C., for 10 minutes or more, more preferably for 30 minutes or more. Further, addition of the sugar phosphate at not less than 1 mM, preferably at 10 to 100 mM, to the above treated fluid can make the nucleoside phosphorylase more stable.

As regards the bacterium without either cytosine or cytidine deaminase activity, a cytidine-deaminase deficient strain of a bacterium belonging to *Bacillus* genus may be used because bacteria belonging to the genus generally have only cytidine deaminase, but not cytosine deaminase. Such a strain is, for example, *Bacillus subtilis* 1A479 available from Bacillus Genetic Stock Center (BGCS). Bacterial cell shaving expressed the nucleoside phosphorylase in such a strain may also be used herein.

The phosphatase deficient strain according to the present invention is exemplified by *E. coli* K-12 DH5α devoid of alkaline phosphatase. Bacterial cells having expressed the cytosine nucleoside phosphorylase in such a strain may also be used herein.

Heat treatment of such bacterial cells may deactivate or decrease acid phosphatase, thereby attaining a higher yield of the product. A suitable heat treatment is conducted under conditions where the bacterial cells, their culture or the processed material thereof is kept standstill or suspended in an aqueous medium at pH 4.0 to 10.0, preferably pH 6.0 to 9.0, at a temperature not lower than 50° C., preferably ranging from 60 to 80° C., for 10 minutes or more, more preferably for 30 minutes or more.

The processing for reducing or removing an inhibitor of the activity of cytosine nucleoside phosphorylase according to the present invention is not limited in particular, provided that the inhibitor can be removed or reduced, but a suitable processing is typically to prepare absolution of the enzyme through ultrasonic disruption of the bacterial cells, and then to add a polar solvent to the enzyme solution in order to precipitate the cytosine nucleoside phosphorylase, or to add ammonium sulfate to the solution in order to salt out and precipitate the enzyme, or to purify it with ion exchange resin.

The reaction for synthesis of the cytosine nucleoside compound according to the present invention is conducted using the bacterial cells, their culture or the processed material thereof, derived from the bacterium that expresses the cytosine nucleoside phosphorylase capable of synthesizing the cytosine nucleoside compound from cytosine or a derivative thereof and the sugar phosphate as substrate, wherein the bacterium-derived matter has lost or is devoid of activity to decompose cytosine or the derivative thereof and the cytosine nucleoside compound, and it may usually be conducted under the conditions of pH 4 to 10 and a temperature ranging from 10 to 80° C. Both concentrations of the sugar phosphate and cytosine or the derivative thereof used in the reaction may range preferably from 0.1 to 1000 mM, and the molar concentration ratio of cytosine or the derivative thereof to the sugar phosphate or its salt should be from 0.1 to 10, preferably about 0.95 taking into account the conversion rate of the reaction.

A metal salt which forms a poorly soluble phosphate salt with phosphoric acid, or a carrier such as ion exchange resin may be added in order to trap phosphoric acid formed in the reaction medium and thereby elevate the reaction yield.

Separation of the cytosine nucleoside compound from the reaction solution may be conducted taking advantage of the solubility difference of the compound against the solvent such as water, or using ion exchange or adsorbent resin.

A trace amount of cytosine remaining in the reaction solution may be eliminated by converting it to uracil, using a bacterium expressing cytosine deaminase which has been processed to reduce or deactivate cytidine deaminase, or using a bacterium created by expression of cytosine deaminase in a bacterial strain devoid of cytidine deaminase.

The procedure of passing the reaction solution through cationic ion exchange resin enables the cytosine nucleoside compound to be separated and purified readily, because uracil that has been formed from remaining cytosine and/or the uracil nucleoside compound that has been formed via decomposition of the cytosine nucleoside compound are not adsorbed by the resin, though only the cytosine nucleoside compound is adsorbed.

EXAMPLES

The present invention will be described in the Examples below, but is not limited by these Examples.

Analytical Procedure:

Analytical Method

Cytosine nucleoside compounds produced were all quantified by means of high performance liquid chromatography. The conditions of analysis are shown in the following.

Column: Develosil ODS-MG-5, 4.6×250 mm (NomuraKagaku)

Column temperature; 40° C.

Pumping flow rate; 1.0 ml/min

Detection; UV 254 nm

Eluate; 50 mM monopotassium phosphate methanol=8:1 (v/v)

Reference Example 1

A Reproducibility Test with Respect to Japanese Patent Laid-Open No. 1-60396)

Synthesis of deoxycytidine was attempted according to Example 1 described in Japanese Patent Laid-Open No. 1-60396. Thus, the 7 bacterial strains deposited, as shown in Table 1, were selected from the group of 24 strains described in the Example 1 and then received. A 50 ml aliquot of a medium (pH 7.0) containing yeast extract at 0.5 g/dl, peptone at 1.0 g/dl, meat extract at 1.0 g/dl and NaCl at 10.5 g/dl was poured into a flask with shoulders of 500 ml by volume and then sterilized. Each of the bacteria, shown in Table 1, that was cultured preliminarily on a nutrient-broth agar medium at 30° C. for 16 hours, was seeded to the above medium with a loop of the cells and shake cultured at 30° C. for 16 hours. The cell mass was separated from the culture solution by centrifugation, then washed with 0.05 M phosphate buffer (pH 7.0) and then centrifuged to prepare the cleaned mass.

The above cleaned mass was added to a solution of 20 mM 2'-deoxyribose-1-phosphate and 20 mM cytosine in 100 ml of 0.05 M tris buffer (pH 7.2) so as to make its concentration at 5 g/dl, and then subjected to the reaction at 60° C. for 24 hours. After the reaction solution was diluted and a portion of the dilution was then analyzed by HPLC, it was found that cytosine as substrate was decomposed to a nearly 100% loss, and that deoxycytidine was not detected.

TABLE 1

| Name of Microbial Strain | Deposition No. |
|---|---|
| *Bacillus* simplex AJ-1357 | FERM P-9533 |
| *Escherichia coli* AJ-11075 | FERM P-9534 |
| *Erwinia carotovora* AJ-2753 | FERM BP-6559 |
| *Pseudomonas roseobubalia* AJ-2384 | FERM P-9471 |
| *Rizobium melioti* AJ-2823 | FERM BP-6565 |
| *Xanthomonas citri* AJ-2785 | FERM BP-6560 |
| *Proteus rettgeri* AJ2770 | FERM BP-941 |

Reference Example 2

PNP Cloning and Creation of a Strain Expressing the Cloned DNA, and Preparation of the Control Cells The genomic DNA from *Escherichia coli* was prepared as follows:

*Escherichia coli* strain K-12/XL-10 (from Stratagene) was seeded into 50 ml of LB medium and cultured at 37° C. overnight, and thereafter the cell mass was collected and then lyzated with a lyzating solution containing lysozyme at 1 mg/ml. The lyzating solution was treated with phenol and then the DNA was precipitated with ethanol as usual. The resulting DNA precipitate was wound around a glass stick for recovery and then washed to use it for PCR.

As primer for PCR, oligonucleotides (entrusted to Hokkaido System Science for synthesis) with the base sequences shown by SEQ ID NOs: 1 and 2, respectively, were used, wherein the base sequences were designed based on the base sequence on the deoD gene (GenBank accession No. AE000508 (with the coding region of BASE NOs. 11531 to 12250)) that codes a known purine nucleoside phosphorylase native to *E. coli*. These primers have the recognition sequences of restriction enzymes EcoRI and HindIII, respectively, near 5'-terminal and 3'-terminal. The PCR was conducted by 30 cycles for the reaction cycle consisting of denaturation at 96° C. for 1 minute, anealing at 55° C. for 1 minute and extension reaction at 74° C. for 1 minute, using 0.1 ml of PCR reaction solution containing 6 ng/μl of the above described genomic DNA from *Escherichia coli*, which has been completely digested by the restriction enzyme HindIII, and 3 μM of each primer.

The above reaction product and plasmid pUC18 (from Takara Shuzo) were digested by EcoRI and HindIII, ligated with Ligation Hi (from Toyobo) and then *E. coli* DH5α was transformed using the resulting recombinant plasmid. The transformant was cultured on a LB agar medium containing 50 μg/ml of ampicillin (Am) and X-Gal (5-bromo-4-chloro-3-indolyl-β-D-galactoside) to obtain the transformant that has become Am resistant and formed white colonies.

The plasmid extracted from the transformant thus obtained and having the DNA fragment of interest inserted was named pUC-PNP73. The base sequence of the DNA fragment inserted in pUC-PNP73 was identified by the common method for determining base sequences. The identified base sequence is shown as SEQ ID NO: 3, while the amino acid sequence translated from the base sequence is shown as SEQ ID NO: 4. The present enzyme has subunits of molecular weight of approximately 26,000 and its activity is known to be expressed in the form of hexamer. The enzyme has the optimum temperature of about 70° C. and the optimum pH range of about 7.0 to 7.5. The transformant thus obtained was named *Escherichia coli* MT-10905.

*Escherichia coli* strain MT-10905 was shake cultured in 100 ml of LB medium containing 50 μg/ml of Am at 37° C. overnight. The culture was centrifuged at 13,000 rpm for 10 min. to obtain the cell mass, which was then suspended in 20 ml of 100 mM tris hydrochloride buffer (pH 8.0). The suspension was centrifuged again at 13,000 rpm for 10 min. to obtain the cell mass, which was then suspended in 2 ml of 100 mM tris hydrochloride buffer (pH 8.0) and 10 mM 2'-deoxyribose-1-phosphate di(monocyclohexylammonium) salt (produced by SIGMA), and frozen and stored at −20° C.

*Escherichia coli* DH5α was transformed using plasmid pUC18 (from Takara Shuzo). This transformant strain was named pUC18/DH5α. The strain pUC18/DH5α was shake cultured in 100 ml of LB medium containing 50 μg/ml of Am at 37° C. overnight. The culture was centrifuged at 13,000 rpm for 10 min. to obtain the cell mass, which was then suspended in 20 ml of 100 mM tris hydrochloride buffer (pH 8.0). The suspension was centrifuged again at 13,000 rpm for 10 min. to obtain the cell mass, which was then suspended in 2 ml of 100 mM tris hydrochloride buffer (pH 8.0) and 10 mM 2'-deoxyribose-1-phosphate di(monocyclohexylammonium) salt (produced by SIGMA), and frozen and stored at −20° C.

Comparative Example 1

Synthesis of Deoxycytidine by the PNP Non-Recombinant *E. coli*

A reaction solution with 1.0 ml by volume consisting of 20 mM 2'-deoxyribose-1-phosphate di(monocyclohexylammonium) salt (produced by SIGMA), 20 mM cytosine (produced by Wako Pure Chemicals, guaranteed grade), 100 mM tris hydrochloride buffer (pH 8.0) and 0.1 ml of the cell mass suspension of the strain pUC18/DH5α obtained in Reference Example 2 was treated at 50° C. for 20 hours. Another solution of the same composition except the absence of the substrates was heat treated similarly and then used as comparative example. When the reaction solution was diluted and then analyzed, deoxycytidine could not be detected. The analysis chart from HPLC of the treated solution for the comparative example is shown in FIG. 1A, and the corresponding chart of the treated reaction solution in FIG. 1B.

Comparative Example 2

Synthesis of Deoxycytidine by the PNP Non-Recombinant *E. coli*

Figure 2:
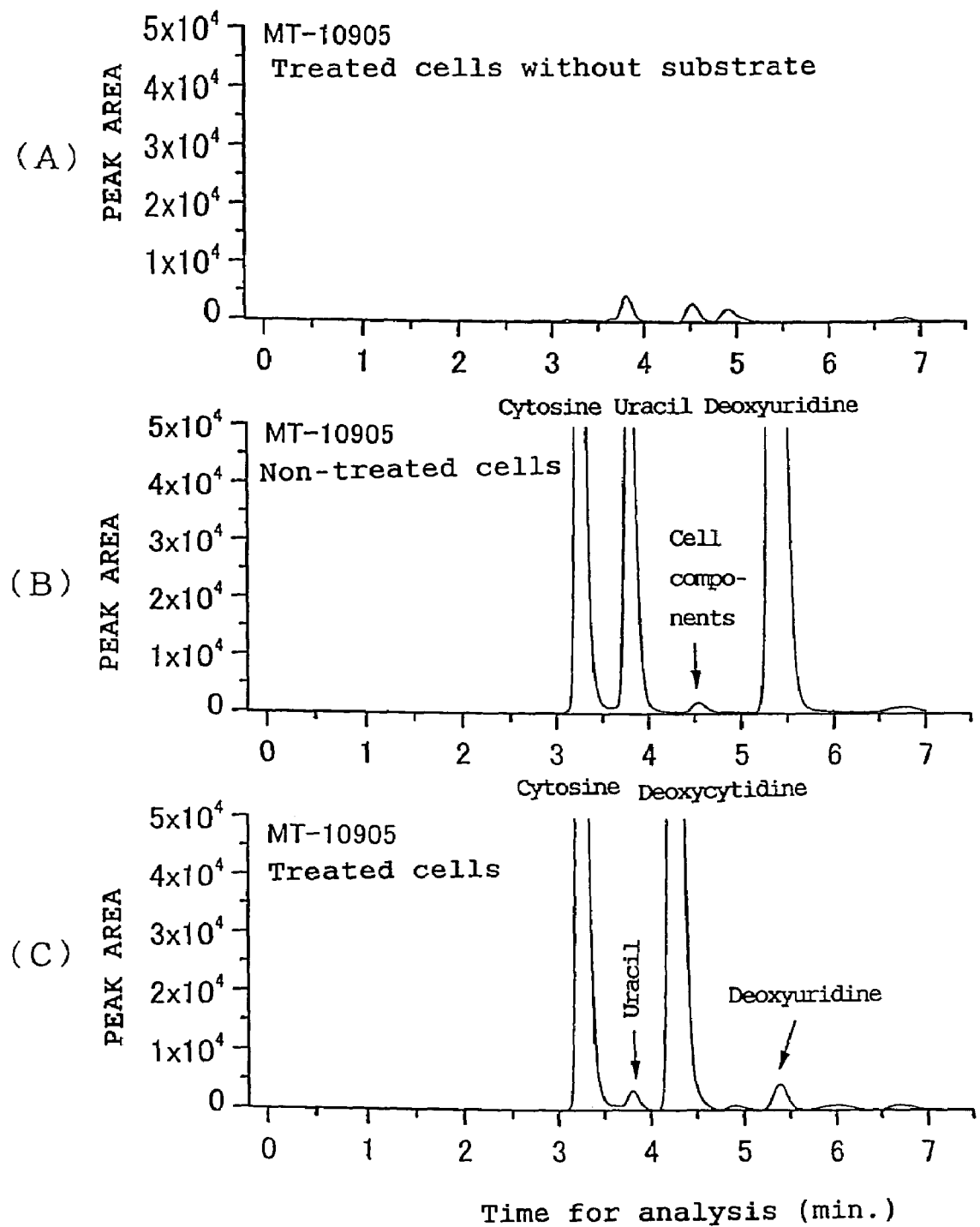
FIG. 2A shows an analytical chart of HPLC in the Comparative Example 2.
FIG. 2B shows an analytical chart of HPLC of a reaction solution in the Comparative Example 2.
FIG. 2C shows an analytical chart of HPLC of Example 5.

A reaction solution with 1.0 ml by volume consisting of 20 mM 2'-deoxyribose-1-phosphate di(monocyclohexylammonium) salt (produced by SIGMA), 20 mM cytosine (produced by Wako Pure Chemicals, guaranteed grade), 100 mM tris hydrochloride buffer (pH 8.0) and 0.1 ml of the cell mass suspension of the strain MT-10905 obtained in Reference Example 2 was treated at 50° C. for 20 hours. Another solution of the same composition except the absence of the substrates was heat treated similarly and then used as comparative example. When the reaction solution was diluted and then analyzed, 10 mM deoxyuridine and 3 mM uracil were produced, but deoxycytidine could not be detected. The analysis chart from HPLC of the treated solution for the comparative example is shown in FIG. 2A, and the corresponding chart of the treated reaction solution in FIG. 2B.

Example 1

Processing with Organic Solvent

To the cell mass suspension of the strain MT-10905 obtained in Reference Example 2 was added a certain amount of methanol so as to attain any one of the methanol concentrations listed in Table 2, and then the suspension was kept at 30° C. for 1 hour. Cytidine deaminase will be expressed as cdd hereafter. The activity of cdd was analyzed after the cell mass suspension was added to 1.0 ml of the reaction solution consisting of 100 mM tris hydrochloride buffer (pH 8.0) and 20 mM cytidine, and then treated at 50° C. for 2 hours.

The cell mass suspension described above was kept at 30° C. for 1 hour without addition of methanol, and then the activity of cdd of the suspension was set at 100% of relative value.

The activity of PNP was analyzed after the cell mass suspension was added to 1.0 ml of the reaction solution consisting of 20 mM 2'-deoxyribose-1-phosphate di(monocyclohexylammonium) salt (produced by SIGMA), 5.4 mM adenine (produced by Wako Pure Chemicals, guaranteed grade) and 100 mM tris hydrochloride buffer (pH 8.0), and then treated at 50° C. or 15 minutes. The above reaction was conducted using such an amount of the cell mass as to produce not more than 2 mM deoxyadenosine. The cell mass suspension described above was kept at 30° C. for 1 hour without addition of methanol, and then the activity of PNP of the suspension was set at 100% of relative value. The results shown in Table 2 reveal that the activity of PNP was reduced minimally, but the activity of cdd was eliminated nearly completely.

TABLE 2

| MeOH (%) | cdd Residual Activity (%) | PNP Residual Activity (%) |
|---|---|---|
| 10 | 80 | 100 |
| 25 | 50 | 99 |
| 50 | 10 | 98 |
| 70 | 0.5 | 97 |
| 90 | 0.1 | 97 |

Example 2

Processing with Organic Solvents

To the cell mass suspension of the strain MT-10905 obtained in Reference Example 2 was added any one of the organic solvents as shown in Table 3, and then the suspension was kept 30° C. for 1 hour.

The results shown in Table 3 reveal that the activity of PNP was reduced minimally, but the activity of cdd was eliminated nearly completely.

TABLE 3

| Type of Organic Solvent | Concentration of Organic Solvent | cdd Activity | PNP Activity |
|---|---|---|---|
| N,N-Dimethylformamide | 50% | 5% | 97% |
| Dimethyl Sulfoxide | 50% | 4% | 96% |
| N,N-Dimethylimidazolidinone | 50% | 4% | 95% |

Example 3

Heat Treatment

The cell mass suspension of the strain MT-10905 obtained in Reference Example 2 was kept at 60° C. Cytosine deaminase will be expressed as cod hereafter. The activity of cod was analyzed after the cell mass suspension was added to 100 mM tris hydrochloride buffer (pH 8.0) and 20 mM cytosine, and then treated at 50° C. for 2 hours. The cod activity of the cell mass suspension that was not heat treated was set at 100% and the remaining activities were expressed with relative values. The results shown in Table 4 reveal that the activity of PNP was reduced minimally, but the activity of cod was eliminated nearly completely.

TABLE 4

| Heating Duration (hr) | cod Residual Activity (%) | PNP Residual Activity (%) |
|---|---|---|
| 0.1 | 90 | 100 |
| 0.2 | 80 | 98 |
| 0.5 | 20 | 98 |
| 2.0 | 2.0 | 98 |
| 20.0 | 0.8 | 97 |

Example 4

Heat Treatment Plus Processing with Organic Solvent

The cell mass suspension heat treated for 20 hours in Example 3 was processed with methanol in the same way as in Example 1. The individual activities of the cell mass suspension that was heat treated for 20 hours in Example 3 were set at 100% and the remaining activities were expressed with relative values. The results shown in Table 5 reveal that the activity of PNP was reduced minimally, but the activities of both cod and cdd were eliminated nearly completely.

TABLE 5

| Concentration of MeOH (%) | cod Residual Activity (%) | cdd Residual Activity (%) | PNP Residual Activity (%) |
|---|---|---|---|
| 10 | 90 | 80 | 100 |
| 25 | 80 | 50 | 98 |
| 50 | 50 | 10 | 96 |
| 70 | 30 | 0.5 | 96 |
| 90 | 10 | 0.1 | 96 |

Example 5

Synthesis of Deoxycytidine by the Recombinant Bacterium Expressing PNP and Treated as in Example 4

1.0 ml of the reaction solution consisting of 20 mM 2'-deoxyribose-1-phosphate di(monocyclohexylammonium) salt (produced by SIGMA), 20 mM cytosine (produced by Wako Pure Chemicals, guaranteed grade), 100 mM tris hydrochloride buffer (pH 8.0) and 0.1 ml of the cell mass suspension processed with 50% methanol in Example 4 was treated at 50° C. for 20 hours. When the reaction solution was diluted and then analyzed, 10.7 mM deoxycytidine, 0.2 mM deoxyuridine and 0.1 mM uracil were produced. The reaction yield was then 53%. The analysis chart from HPLC of the treated solution is shown in FIG. 2C.

Example 6

Synthesis of Deoxycytidine by *Escherichia coli* Treated as in Example 4

1.0 ml of the reaction solution consisting of 20 mM 2'-deoxyribose-1-phosphate di(monocyclohexylammonium) salt (produced by SIGMA), 20 mM cytosine (produced by Wako Pure Chemicals, guaranteed grade), 100 mM tris hydrochloride buffer (pH 8.0) and 0.1 ml of the cell mass suspension of pUC18/DH5α which was obtained in Reference Example 2 and processed with 50% methanol as in Example 4, was treated at 50° C. for 20 hours. When the reaction solution was diluted and then analyzed, 0.14 mM deoxycytidine and 0.17 mM deoxyuridine were produced. The reaction yield was then 0.7%. The analysis chart from HPLC of the treated solution is shown in FIG. 1C.

Example 7

Synthesis of Cytidine by the Recombinant Bacterium Expressing PNP and Treated as in Example 4

1.0 ml of the reaction solution consisting of 20 mM ribose-1-phosphate di(cyclohexylammonium) salt (produced by SIGMA), 20 mM cytosine (produced by Wako Pure Chemicals, guaranteed grade), 100 mM tris hydrochloride buffer (pH 8.0) and 0.1 ml of the cell mass suspension processed with 50% methanol in Example 4 was treated at 50° C. for 20 hours. When the reaction solution was diluted and then analyzed, 5 mM cytidine, 0.1 mM uridine and 0.1 mM uracil were produced. The reaction yield was then 25%.

Example 8

Purification of PNP and Synthesis of Deoxycytidine by the Purified PNP

Figure 3:
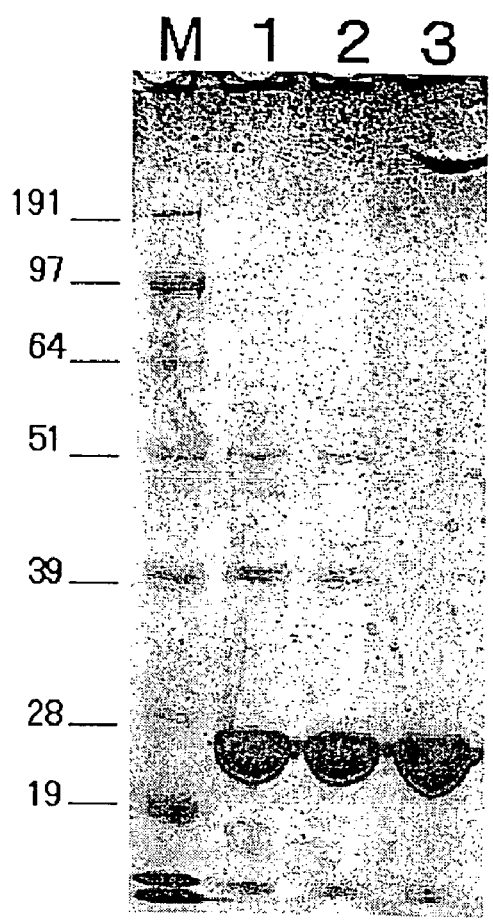
FIG. 3 shows the results in Example 8.

The cell mass obtained in Example 4 was suspended in 10 ml of 10 mM tris hydrochloride buffer (pH 7.5) and disrupted with an ultrasonic disrupter. The disrupted cell suspension was then centrifuged to obtain a crude enzyme solution, which was then added onto a column loaded with DEAE-Toyopearl (3 cm×10 cm: from Toso) that was equilibrated with 50 mM tris hydrochloride buffer (pH 7.5) and then eluted with a linear gradient of 50 mM NaCl to 500 mM NaCl to recover active fractions. The eluate was saturated with 70% aqueous ammonium sulfate to form precipitate, which was then dialyzed against 10 mM tris hydrochloride buffer (pH 7.5). The dialyzed solution was added onto a column loaded with hydroxyapatite (3 cm×15 cm) that was equilibrated with 10 mM tris hydrochloride buffer (pH 7.5) and then eluted with a gradient of 10 mM tris hydrochloride buffer (pH 7.5) to 50 mM tris hydrochloride buffer (pH 7.5) to recover active fractions. The enzyme solution was saturated with 70% aqueous ammonium sulfate to form and recover precipitate, which was then dissolved in 1 ml of 10 mM tris hydrochloride buffer (pH 7.5) and dialyzed against 10 mM tris hydrochloride buffer (pH 7.5) to obtain 2 ml of purified PNP. The purified PNP thus obtained was found to form a single band in electrophoresis using a SDS-polyacrylamide system. The result is shown in FIG. 3.

1.0 ml of the reaction solution consisting of 20 mM 2'-deoxyribose-1-phosphate di(monocyclohexylammonium) salt (produced by SIGMA), 20 mM cytosine (produced by Wako Pure Chemicals, guaranteed grade), 100 mM tris hydrochloride buffer (pH 8.0) and 0.1 ml of the purified PNP was treated at 50° C. for 20 hours. When the reaction solution was diluted and then analyzed, 11.5 mM deoxycytidine was produced and the reaction yield was then 57.5%.

Example 9

Synthesis of Azacytidine by the Recombinant Bacterium Expressing PNP and Treated as in Example 4

1.0 ml of the reaction solution consisting of 20 mM ribose-1-phosphate di(cyclohexylammonium) salt (produced by SIGMA), 20 mM azacytosine (produced by SIGMA), 100 mM tris hydrochloride buffer (pH 8.0) and 0.1 ml of the cell mass suspension processed with 50% methanol in Example 4 was treated at 50° C. for 20 hours. When the reaction solution was diluted and then analyzed, 3.2 mM azacytidine was produced. The reaction yield was then 16%.

Example 10

Synthesis of Fluorocytidine by the Recombinant Bacterium Expressing PNP and Treated as in Example 4

1.0 ml of the reaction solution consisting of 20 mM ribose-1-phosphate di(cyclohexylammonium) salt (produced by SIGMA), 20 mM 5-fluorocytosine (produced by SIGMA), 100 mM tris hydrochloride buffer (pH 8.0) and 0.1 ml of the cell mass suspension processed with 50% methanol in Example 4 was treated at 50° C. for 20-hours. When the reaction solution was diluted and then analyzed, 2.4 mM 5-fluorocytidine was produced. The reaction yield was then 12%.

Example 11

Synthesis of Methylcytidine by the Recombinant Bacterium Expressing PNP and Treated as in Example 4

1.0 ml of the reaction solution consisting of 20 mM ribose-1-phosphate di(cyclohexylammonium) salt (produced by SIGMA), 20 mM 5-methylcytosine (produced by SIGMA), 100 mM tris hydrochloride buffer (pH 8.0) and 0.1 ml of the cell mass suspension processed with 50% methanol in Example 4 was treated at 50° C. for 20 hours. When the reaction solution was diluted and then analyzed, 2.1 mM 5-methylcytidine was produced. The reaction yield was then 10.5%.

Example 12

Synthesis of Deoxycytidine by Bacterial Mass Devoid of Degrading Activity with PNP Incorporated (1) Creation of *Escherichia coli-Bacillus subtilis* shuttle vectors pPNP04 and pPNP05 for expressing *E. coli* PNP in *B. subtilis*

The PCR using pUC-PNP73 as template and the synthetic oligonucleotide primer of SEQ ID NOs: 5 and 6 allowed the gene for purine nucleoside phosphorylase of *Escherichia coli* to be amplified, resulting in production of 0.8 kb DNA fragment A. Then, by the PCR which used pNP150 (FERM BP-425) described in Japanese Patent Laid-Open No. 60-210986 as template and the synthetic oligonucleotide primer of SEQ ID NOs: 7 and 8, the region including the transcription promoter and translation regulating site derived from the neutral protease of *Bacillus amyloliquefaciens* was amplified, resulting in production of 1.0 kb DNA fragment B. Then, annealing was carried out using overlapping regions of DNA fragments A and B. The PCR using the resulting fragment as template and the synthetic oligonucleotide primer of SEQ ID NOs: 6 and 7 allowed approximately 1.8 kb DNA fragment C to be produced via amplification. This DNA fragment C was digested by the restriction enzymes EcoRI and HindIII to produce insert fragments. *Escherichia coli-Bacillus subtilis* shuttle vectors pRB373 and pRB374 were received from Bacillus Genetic Stock Center (BGSC; OH) and then each digested by the restriction enzymes EcoRI and HindIII to prepare vector fragments. The vector fragments were ligated in the presence of an excessive amount of the above insert fragments to create shuttle vectors pPNP04 and pPNP05 expressing the purine nucleoside phosphorylase of *E. coli*.

(2) Entry of pPNP04 and pPNP05 into *Bacillus subtilis*, and synthesis of deoxycytidine using the transformant

*Bacillus subtilis* strains 1A479 and 1A480, both devoid of cytidine deaminase activity, were received from *Bacillus* Genetic Stock Center (BGSC; OH).

Transformation with plasmids pPNP04 and pPNP05 obtained in procedure (1) was conducted according to the protoplast method by Chang (Chang, S. and Cohen, S. N.; Mol. Gen. Genet. 168,111(1978)) to obtain transformants 1A480 (pPNP04), 1A480 (pPNP05), 1A479 (pPNP4) and 1A479 (pPNP05).

Then, the strain 1A480 (pPNP04) was evaluated for activity of deoxycytidine synthesis as follows:

The strain 1A480 (pPNP04) was cultured in 20 ml of the L medium of two-fold concentration at 35° C. for 17 hours. 1.5 ml of the culture was centrifuged to obtain the cell mass, which was then frozen and stored at −20° C. 11.0 ml of a reaction solution consisting of 24 mM 2'-deoxyribose-1-phosphate di(monocyclohexylammonium) salt (produced by SIGMA), 20 mM cytosine (produced by Wako Pure Chemicals, guaranteed grade) and 100 mM tris hydrochloride buffer (pH 8.0) was added to 0.1 ml of the frozen cell mass and shaken at 50° C. The solution was sampled 1.5 hours and 18 hours after the start. The samples were diluted with water by 20 fold and centrifuged to remove the cell mass. The supernatants thereof were analyzed by HPLC to reveal that accumulation of deoxycytidine was from 1.4 to 1.5 mM after 1.5 hours and from 6.4 to 7.0 mM after 18 hours, while no degradation of either the substrates or the product was detected.

Analysis of deoxycytidine synthesis by the strains 1A480 (pPNP05), 1A479 (pPNP04) and 1A479 (pPNP05) revealed that they were as effective as the strain 1A480 (pPNP04) for deoxycytidine synthesis.

Example 13

Obtainment of Enzymes Substituted by an Amino Acid but Keeping Cytosine Nucleoside Phosphorylase Activity Mutagenesis was introduced using the plasmid DNA of pUC-PNP73 obtained in Reference Example 2 as template and Quick Change Site-Directed Mutagenesis Kit from STRATAGENE, which will be referred to simply as Kit hereafter. The examples below basically followed the principle and procedure of the Kit.

10 ml of a LB liquid medium was prepared in a 30-ml test tube and then sterilized in an autoclave at 121° C. for 20 minutes. A certain amount of ampicillin was added to the medium so as to set its final concentration at 100 μg/ml. The strain MT-10905 obtained in Reference Example 2 was seeded by a loop of the cell mass and then cultured at 37° C. and 300 rpm for about 20 hours. Then, 1-ml aliquots of the culture were poured into any suitable centrifuge tubes to separate the cell mass by centrifugation (at 15,000 rpm for 5 minutes). After that, the plasmid DNA of pUC-PNP73 was prepared from the cell mass by the alkaline SDS extraction.

The PCR was carried out using the plasmid DNA of pUC-PNP73 as template, and the respective DNAs of SEQ ID NOs: 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, and 45 and 46 as primers. The composition of the PCR medium is shown in Table 6. The conditions of amplification are shown in Table 7.

The restriction enzyme DpnI was added to the above PCR medium by 4 units and maintained at 37° C. for 1 hour. 1 μl of the reaction medium was added to 100 μl of the competent cells (from Toyobo) of *E. coli* K-12DH5α, and maintained in ice for 30 minutes. Then, the cell suspension was immersed in a thermostatic water bath at 42° C. for 30 seconds. 0.9 ml of the NZY+ medium, which is an accessory to the competent cells, was added to the cell suspension and shaken at 37° C. for 1 hour.

The above culture was smeared onto LB agar medium where a certain amount of ampicillin had been added so as to set its final concentration at 100 μg/ml, and then maintained at 37° C. for 20 hours to form colonies.

Five clones were arbitrarily selected from the colonies, seeded by a loop of each cell mass in 100 ml of LB medium containing 50 μg/ml of Am and shake cultured at 37° C. overnight. The culture was centrifuged at 13,000 rpm for 10 minutes to obtain the cell mass, which was then suspended in 20 ml of 100 mM tris hydrochloride buffer (pH 8.0). The suspension was centrifuged again at 13,000 rpm for 10 minutes to obtain the cell mass, which was then suspended in 2 ml of 100 mM tris hydrochloride buffer (pH 8.0) and 10 mM 2'-deoxyribose-1-phosphate di(monocyclohexylammonium) salt (produced by SIGMA), processed as in Example 4 and subjected to the reaction for deoxycytidine synthesis as in Example 5. Analysis of deoxycytidine by HPLC revealed that four of the five clones produced deoxycytidine, thus holding the activity of cytosine nucleoside phosphorylase.

The cell mass of each of the above four clones was separated from 1 ml of the above culture remaining after analysis of the activity of cytosine nucleoside phosphorylase. The plasmid DNA of each of the four clones was prepared from the cell mass by alkaline SDS extraction. The base sequences of the DNA fragments were identified by the common method for determining base sequences. Enzyme activity was measured as in Example 1. A list of the results is shown in Table 8.

TABLE 6

| | |
|---|---|
| Template Plasmid | 2 μL (5 μg/mL) |
| Primer (Sense Chain) | 1.25 μL (100 μg/mL) |
| Primer (Antisense Chain) | 1.25 μL (100 μg/mL) |
| Added Buffer | 5 μL |
| Added dNTP | 1 μL (5 μg/mL) |
| H$_2$0 | 39.5 μL |
| Enzyme | 1 μL |

TABLE 7

| Cycle | Temperature | Period of Time |
|---|---|---|
| 1 | 95° C. | 30 sec. |
| 2 | 95° C. | 30 sec. |
| 3 | 55° C. | 1 min. |
| 4 | 68° C. | 6 min., then returns to Cycle 2 (12 times) |

TABLE 8

Base Sequences of the Obtained Genes and Activities

| No. of Amino Acid | Native Base | Native Amino Acid | Modified Base | Modified Amino Acid | Activity |
|---|---|---|---|---|---|
| 10 | atg | methionine | gca | alanine | + |
| 16 | gta | valine | gca | alanine | + |
| 42 | aac | arginine | ctg | leucine | + |
| 54 | aaa | lysine | tcc | serine | + |
| 67 | atc | isoleucine | ctg | leucine | + |
| 74 | acc | threonine | gcc | alanine | + |
| 104 | gtc | valine | atc | isoleucine | + |
| 135 | gtg | valine | atg | methionine | + |
| 157 | gct | alanine | tcc | serine | + |
| 167 | atg | methionine | acg | threonine | + |
| 168 | ttc | Phenyl alanine | tcc | serine | + |
| 178 | ggc | glycine | gca | alanine | + |
| 179 | gtg | valine | acc | threonine | + |
| 183 | gcg | alanine | tcc | serine | + |
| 199 | acc | threonine | gca | alanine | + |
| 204 | tct | serine | ttt | Phenyl alanine | + |
| 210 | cac | histidine | ctg | leucine | + |
| 228 | atc | isoleucine | tcc | serine | + |
| 233 | gtt | valine | ctg | leucine | + |

Reference Example 3

Transformation of *Escherichia coli* K-12 W3110

*Escherichia coli* strain K-12 W3110 (ATCC27325) was transformed with the plasmid pUC-PNP73 obtained in Reference Example 2 according to the common procedure. The transformant thus obtained was named MT-10948. When the transformant was cultured as in Reference Example 2, it was twice as active as the corresponding transformant of *Escherichia coli* strain K-12 DH5α.

Example 14

Removal of Reaction Inhibitors Through Precipitation with Polar Solvent

The cell mass of the strain MT-10948 cultured as in Reference Example 2 was disrupted with an ultrasonic disrupter. The same volume of acetone as the disruption fluid was added to the fluid, which was then centrifuged to remove the precipitate.

Then, a half volume of acetone compared to the above was added to the above supernatant formed by centrifugation and centrifuged to recover the precipitate.

The recovered precipitate was dried up in a vacuum dryer. The dried precipitate was dissolved in 2 ml of 100 mM tris hydrochloride buffer (pH 8.0) and 10 mM 2'-deoxyribose-1-phosphate di(monocyclohexylammonium) salt (produced by SIGMA) and then processed as in Example 4. A 2-ml solution of the enzyme fractionated with acetone was added to water (105.3 g) together with cytosine (6.96 g), 2'-deoxyribose-1-phosphate diammonium salt (18.7 g) and magnesium hydroxide (6.2 g), and the reaction took place at 50° C. for 24 hours. The HPLC analysis after the reaction demonstrated that 11.4 g (80%) of 2'-deoxycytidine was produced. For comparison, a 2-ml fluid containing disrupted cell mass before addition of acetone was similarly subjected to the reaction. As a result, 8.5 g (60%) of 2'-deoxycytidine was produced.

Example 15

Removal of Reaction Inhibitors Through Precipitation with Ammonium Sulfate

The cell mass of the strain MT-10948 cultured as in Reference Example 2 was disrupted with an ultrasonic disrupter.

Ground pieces of ammonium sulfate were slowly added to the disruption fluid so as to attain 40% saturation finally. The fluid was slowly agitated in ice for 1 hour and centrifuged to remove the precipitate. Similarly, ground pieces of ammonium sulfate were added to the supernatant formed by centrifugation so as to attain 70% saturation finally. The fluid was slowly agitated in ice for 1 hour and centrifuged to obtain the precipitate. The precipitate was then dissolved in 2 ml of 100 mM tris hydrochloride buffer (pH 8.0) and 10 mM 2'-deoxyribose-1-phosphate di(monocyclohexylammonium) salt (produced by SIGMA). The solution was processed as in Example 4 and subjected to the reaction for deoxycytidine synthesis as in Example 14. As a result, 11.0 g (80%) of 2'-deoxycytidine was produced.

Example 16

Removal of Reaction Inhibitors: Purified Enzyme in Example 8

A 2-ml solution of the enzyme obtained as in Example 8 was subjected to the reaction for deoxycytidine synthesis as in Example 14. As a result, 11.0 g (80%) of 2'-deoxycytidine was produced.

Example 17

The Effect of a phoA Deficient Strain

A 2-ml suspension of the cell mass obtained in Example 4 was subjected to the same reaction as in Example 14. As a result, 11.0 g (80%) of 2'-deoxycytidine was produced. On the other hand, when the strain MT-10948 was processed as in Example 4, this strain was twice as high as the strain MT-10905 for activity. However, when this strain was subjected to the same reaction as in Example 14, only 8.5 g (60%) of 2'-deoxycytidine was produced.

Example 18

To the mixture of water (96.4 g) and 4.8 g of cyclohexane, were added 6.96 g (62.6 mmol) of cytosine, 18.7 g (75.4 mmol) of 2'-deoxyribose-1-phosphate diammonium salt, 7.58 g (132 mmol) of magnesium hydroxide and the frozen cell mass (2.0 g) prepared in Reference Example 3. The reaction took place at 45° C. for 18 hours, controlling the solution at pH 8.8 with acetic acid. The HPLC analysis after the reaction demonstrated that 10.03 g (70.5 mol %/cytosine) of 2'-deoxycytidine was produced as object compound. At the same time, 0.73 g (10.4 mol %/cytosine) of uracil and 1.80 g (12.6 mol %/cytosine) of 2'-deoxyuridine were produced as byproduct, respectively.

Example 19

Synthesis of 2'-deoxycytidine was carried out under the same conditions as in Example 18, except that the solvent for processing the cell mass and/or the solvent added for the reaction were different. The results are shown in Tables 9 and 10.

TABLE 9

Example 19

Reaction Procedure

| Solvent Added in Enzyme Treatment | Solvent Added in Reaction | Reaction Yield (%) | | |
|---|---|---|---|---|
| | | 2'-Deoxycytidine | Uracil | 2'-Deoxyuridine |
| No solvent | toluene | 70.1 | 10.82 | 12.9 |
| No solvent | ethylbenzene | 73.8 | 9.7 | 8.9 |
| DMF | cyclohexane | 88.9 | 3.6 | 0.4 |
| DMF | toluene | 86.7 | 4.3 | 0.9 |
| DMF | ethylbenzene | 94.8 | 1.4 | 0.6 |

TABLE 10

Comparative Example

Reaction Procedure

| Solvent Added in Enzyme Treatment | Solvent Added in Reaction | Reaction Yield (%) | | |
|---|---|---|---|---|
| | | 2'-Deoxycytidine | Uracil | 2'-Deoxyuridine |
| None | None | 0 | 12.6 | 58.7 |

Example 20

Synthesis of 2'-deoxycytidine

To 20 g of pure water were added 20 ml (total exchange capacity 24 mmol) of strongly basic anionic exchange resin (Levatit MP500: exchange capacity 1.1 eq/L) and 2-deoxyribose-1-phosphate diammonium salt (4.96 g, 20 mmol), and the mixture was stirred at room temperature for 30 minutes. Then, enzyme solution (0.5 ml), prepared according to Example 4, and cytosine (2.11 g, 19 mmol) were added to the mixture, which was stirred at 50° C. for 10 hours. Analysis of the reaction mixture by HPLC revealed that 2'-deoxycytidine, the desired product was produced in the yield of 80%.

Production of a nucleoside compound using a nucleoside phosphorylase may be conducted both regiospecifically and stereospecifically under mild conditions. It is thus hoped that an industrial method of production will be established, but it is not attained yet. The present invention provides a method for producing a cytosine nucleoside compound from pentose-1-phosphate and cytosine or a derivative thereof using a nucleoside phosphorylase reactive to cytosine. The invention also provides a method for specifically reducing an activity to degrade the substrates or the product, resulting in efficient production of the cytosine nucleoside compound.

What is claimed is:

1. A method for producing a cytosine nucleoside compound comprising reacting a sugar phosphate and cytosine or a derivative of cytosine in the presence of an enzyme preparation obtained from a bacterial mass of *Escherichia coli* or culture thereof having a purine nucleoside phosphorylase, which acts also as a cytosine nucleoside phosphorylase, to obtain the cytosine nucleoside compound, wherein, before the step of reacting a sugar phosphate and cytosine or a derivative of cytosine, the activity of cytosine deaminase and/or the activity of cytidine deaminase of said bacterial mass, or culture thereof or said enzyme preparation are lost or reduced by at least one of the following steps:

(i) contacting the bacterial mass, culture thereof or an enzyme preparation having the activity of purine nucleotide phosphorylase and at least one of the activities of cytosine deaminase and cytidine deaminase with water containing N,N-dimethylformamide or N,N'-dimethylimidazolidinone as an organic solvent at a concentration of 50 volume % to 90 volume %, for an effective time of at least 1 hour, in the presence of a pentose-1-phosphate, to eliminate or reduce selectively at least one of the activities of cytosine deaminase and the activity of cytidine deaminase; and (ii) heating the bacterial mass, culture thereof or enzyme preparation at a temperature from 60° C. to 90° C. for an effective time of at least 30 minutes, in the presence of a pentose-1-phosphate, to eliminate or reduce selectively at least one of the activities of cytosine deaminase and the activity of cytidine deaminase, wherein the enzyme preparation is obtained from the bacterial mass or culture thereof thus treated by at least one of steps (i) and (ii)

wherein said derivative of cytosine is a compound expressed by formula (I)

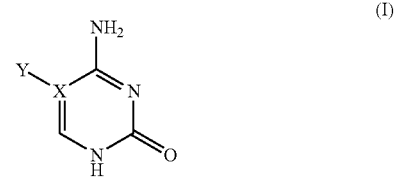

wherein X is carbon or nitrogen, Y is hydrogen, a halogen or a lower alkyl; and wherein the purine nucleoside phosphorylase has an activity of catalyzing a reaction between a compound of formula (I) and a sugar phosphate to produce a corresponding cytosine nucleoside compound.

2. The method according to claim 1, wherein said sugar phosphate is ribose-1-phosphate, 2-deoxyribose-1-phosphate, 2',3'-dideoxyribose-1-phosphate or dioxolane sugar phosphate.

3. The method according to claim 1, wherein the enzyme preparation is obtained from any one of:

a) disrupting the bacterial mass thus treated by at least one of the steps (i) and (ii) to obtain a disruption fluid and obtaining the enzyme preparation as precipitate from the disruption fluid by use of a polar solvent, or b) disrupting the bacterial mass thus treated by at least one of the steps (i) and (ii) to obtain a disruption fluid and obtaining the enzyme preparation as precipitate from the disruption fluid by use of salting out, or c) disrupting the bacterial mass thus treated by at least one of the steps (i) and (ii) to obtain a disruption fluid and separating an enzyme fraction including the purine nucleoside phosphorylase from the disruption fluid by use of an ion exchange resin;

wherein an inhibitor of the activity of cytosine nucleoside phosphorylase is reduced or removed.

* * * * *

```
                        SEQUENCE LISTING

<160> NUMBER OF SEQ ID NOS: 46

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide to act as a PCR primer for
      cloning of purine nucleoside phophrylase of E. coli K-12

<400> SEQUENCE: 1
gtgaattcac aaaaaggata aaacaatggc                                      30

<210> SEQ ID NO 2
<211> LENGTH: 29
<212> TYPE: DNA
<213> ORGANISM: Artificial Sequence
<220> FEATURE:
<223> OTHER INFORMATION: Oligonucleotide to act as a PCR primer for
      cloning of purine nucleoside phophrylase of E.coli K-12

<400> SEQUENCE: 2
tcgaagcttg cgaaacacaa ttactcttt                                       29

<210> SEQ ID NO 3
<211> LENGTH: 720
<212> TYPE: DNA
<213> ORGANISM: Escherichia coli

<400> SEQUENCE: 3
atggctaccc cacacattaa tgcagaaatg ggcgatttcg ctgacgtagt tttgatgcca     60
ggcgacccgc tgcgtgcgaa gtatattgct gaaactttcc ttgaagatgc ccgtgaagtg    120
```

-continued

```
aacaacgttc gcggtatgct gggcttcacc ggtacttaca aaggccgcaa aatttccgta    180
atgggtcacg gtatgggtat cccgtcctgc tccatctaca ccaaagaact gatcaccgat    240
ttcggcgtga agaaaattat ccgcgtgggt tcctgtggcg cagttctgcc gcacgtaaaa    300
ctgcgcgacg tcgttatcgg tatgggtgcc tgcaccgatt ccaaagttaa ccgcatccgt    360
tttaaagacc atgactttgc cgctatcgct gacttcgaca tggtgcgtaa cgcagtagat    420
gcagctaaag cactgggtat tgatgctcgc gtgggtaacc tgttctccgc tgacctgttc    480
tactctccgg acggcgaaat gttcgacgtg atggaaaaat acggcattct cggcgtggaa    540
atggaagcgg ctggtatcta cggcgtcgct gcagaatttg gcgcgaaagc cctgaccatc    600
tgcaccgtat ctgaccacat ccgcactcac gagcagacca ctgccgctga gcgtcagact    660
accttcaacg acatgatcaa aatcgcactg gaatccgttc tgctgggcga taaagagtaa    720
```

<210> SEQ ID NO 4
<211> LENGTH: 239
<212> TYPE: PRT
<213> ORGANISM: Escherichia coli

<400> SEQUENCE: 4

```
Met Ala Thr Pro His Ile Asn Ala Glu Met Gly Asp Phe Ala Asp Val
1               5                  10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```

<210> SEQ ID NO 5
<211> LENGTH: 42
<212> TYPE: DNA
<213> ORGANISM: Artificial Sequence
<220> FEATURE:

<223> OTHER INFORMATION: Oligonucleotide to act as a PCR primer

<400> SEQUENCE: 5
cattattttc aaaaggggg atttattatg gctaccccac ac    42

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 6
cagaagcttg cgaaacacaa ttac    24

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 7
tttgaattcc ttagtgcttt catagattaa act    33

<210> SEQ ID NO 8
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 8
ttctgcatta atgtgtgggg tagccataat aaatccccct tt    42

<210> SEQ ID NO 9
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 9
ccacacatta atgcagaagc aggcgatttc gct    33

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 10
agcgaaatcg cctgcttctg cattaatgtg tgg    33

<210> SEQ ID NO 11
<211> LENGTH: 41
<212> TYPE: DNA
<213> ORGANISM: Artificial Sequence
<220> FEATURE:
<223> OTHER INFORMATION: Oligonucleotide to act as a PCR primer

<400> SEQUENCE: 11
cttgaagatg cccgtgaagt gaacctggtt cgcggtatgc t    41

```
<210> SEQ ID NO 12
<211> LENGTH: 41
<212> TYPE: DNA
<213> ORGANISM: Artificial Sequence
<220> FEATURE:
<223> OTHER INFORMATION: Oligonucleotide to act as a PCR primer

<400> SEQUENCE: 12
agcataccgc gaaccaggtt cacttcacgg gcatcttcaa g                          41

<210> SEQ ID NO 13
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 13
ctgggcttca ccggtactta ctccggccgc aaaatttccg ta                         42

<210> SEQ ID NO 14
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 14
tacggaaatt ttgcggccgg agtaagtacc ggtgaagccc ag                         42

<210> SEQ ID NO 15
<211> LENGTH: 40
<212> TYPE: DNA
<213> ORGANISM: Artificial Sequence
<220> FEATURE:
<223> OTHER INFORMATION: Oligonucleotide to act as a PCR primer

<400> SEQUENCE: 15
atgggtcacg gtatgggtct gccgtcctgc tccatctaca                            40

<210> SEQ ID NO 16
<211> LENGTH: 40
<212> TYPE: DNA
<213> ORGANISM: Artificial Sequence
<220> FEATURE:
<223> OTHER INFORMATION: Oligonucleotide to act as a PCR primer

<400> SEQUENCE: 16
tgtagatgga gcaggacggc agacccatac cgtgacccat                            40

<210> SEQ ID NO 17
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 17
cgcgtgggta acctgttctc ctccgacctg ttctactctc cg                         42

<210> SEQ ID NO 18
<211> LENGTH: 42
<212> TYPE: DNA
<213> ORGANISM: Artificial Sequence
<220> FEATURE:
<223> OTHER INFORMATION: Oligonucleotide to act as a PCR primer
```

-continued

```
<400> SEQUENCE: 18
cggagagtag aacaggtcgg aggagaacag gttacccacg cg                    42

<210> SEQ ID NO 19
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 19
atggaaaaat acggcattct cgcagtggaa atggaagcgg ct                    42

<210> SEQ ID NO 20
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 20
agccgcttcc atttccactg cgagaatgcc gtattttcc at                     42

<210> SEQ ID NO 21
<211> LENGTH: 41
<212> TYPE: DNA
<213> ORGANISM: Artificial Sequence
<220> FEATURE:
<223> OTHER INFORMATION: Oligonucleotide to act as a PCR primer

<400> SEQUENCE: 21
aaatacggca ttctcggcac cgaaatggaa gcggctggta t                     41

<210> SEQ ID NO 22
<211> LENGTH: 41
<212> TYPE: DNA
<213> ORGANISM: Artificial Sequence
<220> FEATURE:
<223> OTHER INFORMATION: Oligonucleotide to act as a PCR primer

<400> SEQUENCE: 22
ataccagccg cttccatttc ggtgccgaga atgccgtatt t                     41

<210> SEQ ID NO 23
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 23
gtatctgacc acatccgcac tctggagcag accactgccg ct                    42

<210> SEQ ID NO 24
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 24
agcggcagtg gtctgctcca gagtgcggat gtggtcagat ac                    42

<210> SEQ ID NO 25
<211> LENGTH: 42
```

<212> TYPE: DNA
<213> ORGANISM: Artificial Sequence
<220> FEATURE:
<223> OTHER INFORMATION: Oligonucleotide to act as a PCR primer

<400> SEQUENCE: 25
accttcaacg acatgatcaa atccgcactg gaatccgttc tg                42

<210> SEQ ID NO 26
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 26
cagaacggat tccagtgcgg atttgatcat gtcgttgaag gt                42

<210> SEQ ID NO 27
<211> LENGTH: 41
<212> TYPE: DNA
<213> ORGANISM: Artificial Sequence
<220> FEATURE:
<223> OTHER INFORMATION: Oligonucleotide to act as a PCR primer

<400> SEQUENCE: 27
atcaaaatcg cactggaatc cctgctgctg ggcgataaag a                 41

<210> SEQ ID NO 28
<211> LENGTH: 41
<212> TYPE: DNA
<213> ORGANISM: Artificial Sequence
<220> FEATURE:
<223> OTHER INFORMATION: Oligonucleotide to act as a PCR primer

<400> SEQUENCE: 28
tctttatcgc ccagcagcag ggattccagt gcgattttga t                 41

<210> SEQ ID NO 29
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 29
attctcggcg tggaaatgga atccgctggt atctacggcg tc                42

<210> SEQ ID NO 30
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 30
gacgccgtag ataccagcgg attccatttc cacgccgaga at                42

<210> SEQ ID NO 31
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 31
gaatttggcg cgaaagccct ggcaatctgc accgtatctg ac            42

<210> SEQ ID NO 32
<211> LENGTH: 42
<212> TYPE: DNA
<213> ORGANISM: Artificial Sequence
<220> FEATURE:
<223> OTHER INFORMATION: Oligonucleotide to act as a PCR primer

<400> SEQUENCE: 32
gtcagatacg gtgcagattg ccagggcttt cgcgccaaat tc            42

<210> SEQ ID NO 33
<211> LENGTH: 39
<212> TYPE: DNA
<213> ORGANISM: Artificial Sequence
<220> FEATURE:
<223> OTHER INFORMATION: Oligonucleotide to act as a PCR primer

<400> SEQUENCE: 33
tactctccgg acggcgaaac gttcgacgtg atggaaaaa               39

<210> SEQ ID NO 34
<211> LENGTH: 39
<212> TYPE: DNA
<213> ORGANISM: Artificial Sequence
<220> FEATURE:
<223> OTHER INFORMATION: Oligonucleotide to act as a PCR primer

<400> SEQUENCE: 34
tttttccatc acgtcgaacg tttcgccgtc cggagagta               39

<210> SEQ ID NO 35
<211> LENGTH: 39
<212> TYPE: DNA
<213> ORGANISM: Artificial Sequence
<220> FEATURE:
<223> OTHER INFORMATION: Oligonucleotide to act as a PCR primer

<400> SEQUENCE: 35
tctccggacg gcgaaatgtc cgacgtgatg gaaaaatac               39

<210> SEQ ID NO 36
<211> LENGTH: 39
<212> TYPE: DNA
<213> ORGANISM: Artificial Sequence
<220> FEATURE:
<223> OTHER INFORMATION: Oligonucleotide to act as a PCR primer

<400> SEQUENCE: 36 gtattttttcc atcacgtcgg acatttcgcc gtccggaga              39

<210> SEQ ID NO 37
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 37
ggcgatttcg ctgacgcagt tttgatgcca ggcgac                  36

<210> SEQ ID NO 38
<211> LENGTH: 36
<212> TYPE: DNA
<213> ORGANISM: Artificial Sequence

```
<220> FEATURE:
<223> OTHER INFORMATION: Oligonucleotide to act as a PCR primer

<400> SEQUENCE: 38
gtcgcctggc atcaaaactg cgtcagcgaa atcgcc                               36

<210> SEQ ID NO 39
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 39
accatctgca ccgtatttga ccacatccgc actcac                               36

<210> SEQ ID NO 40
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 40
gtgagtgcgg atgtggtcaa atacggtgca gatggt                               36

<210> SEQ ID NO 41
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 41
ccgtcctgct ccatctacgc caaagaactg atcacc                               36

<210> SEQ ID NO 42
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 42
ggtgatcagt tctttggcgt agatggagca ggacgg                               36

<210> SEQ ID NO 43
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 43
atcgctgact tcgacatgat gcgtaacgca gtagat                               36

<210> SEQ ID NO 44
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 44
atctactgcg ttacgcatca tgtcgaagtc agcgat                               36
```

```
<210> SEQ ID NO 45
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 45
gtaaaactgc gcgacatcgt tatcggtatg ggtgcc                              36

<210> SEQ ID NO 46
<211> LENGTH: 36
<212> TYPE: DNA
<213> ORGANISM: Artificial Sequence
<220> FEATURE:
<223> OTHER INFORMATION: Oligonucleotide to act as a PCR primer

<400> SEQUENCE: 46
ggcacccata ccgataacga tgtcgcgcag ttttac                              36
```